(12) United States Patent
Böttcher et al.

(10) Patent No.: US 6,197,977 B1
(45) Date of Patent: Mar. 6, 2001

(54) PROCESS FOR THE PREPARATION OF L-ASCORBIC ACID

(75) Inventors: Andreas Böttcher, Nussloch; Hans Gurski, Frankenthal; Thomas Kuntze, Böhl-Iggelheim, all of (DE); Karsten Kjaergaard, Grenaa (DK)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/553,896

(22) Filed: Apr. 20, 2000

(30) Foreign Application Priority Data

Apr. 28, 1999 (DE) .............................................. 199 19 203

(51) Int. Cl.[7] .................................................. C07D 307/62
(52) U.S. Cl. ............................................................. 549/315
(58) Field of Search ............................................... 549/315

(56) References Cited

U.S. PATENT DOCUMENTS

| | | | |
|---|---|---|---|
| 2,185,383 | 1/1940 | Paternack et al. | 260/344 |
| 5,391,770 | 2/1995 | LeFur et al. | 549/315 |
| 5,744,618 | 4/1998 | Fechtel et al. | 549/315 |
| 5,744,634 | 4/1998 | Veits | 560/174 |

FOREIGN PATENT DOCUMENTS

| | | |
|---|---|---|
| 195 47 073 C1 | 11/1996 | (DE) . |
| 0 671 405 A1 | 9/1995 | (EP) . |
| 48-15931 | 3/1973 | (JP) . |
| 50-022113 | 7/1975 | (JP) . |
| 58-177986 | 10/1983 | (JP) . |
| WO 87/00839 | 2/1987 | (WO) . |
| WO 99/07691 | 2/1999 | (WO) . |

OTHER PUBLICATIONS

Crawford et al. "Synthesis of L–Ascorbic Acid" Advances in Carbohydrate Chemistry and Biochemistry, vol. 37(1980) pp. 79–155.

Ullmann's Encyclopedia of Industrial Chemisty, vol. A 27, (1996) pp. 551–557.

*Primary Examiner*—Amelia Owens
(74) *Attorney, Agent, or Firm*—Keil & Weinkauf

(57) ABSTRACT

The invention relates to a process for the preparation of L-ascorbic acid, which comprises lactonizing a melt of alkyl 2-keto-L-gulonate under acidic conditions.

13 Claims, No Drawings

PROCESS FOR THE PREPARATION OF L-ASCORBIC ACID

The invention relates to a process for the preparation of L-ascorbic acid, in which a melt of $C_3$–$C_{10}$-alkyl 2-keto-L-gulonate is lactonized under acidic conditions.

In the past, a large number of process variants for the preparation of L-ascorbic acid have been published. A review is found, inter alia, in Crawford et al., Adv. Carbohydrate Chem. 37, 79 (1980) and in Ullmann's Encyclopedia of Industrial Chemistry, Vol. A27, 551–557 (1996).

A number of processes for the preparation of ascorbic acid by reaction of 2-keto-L-gulonic acid with an acid are known.

Thus, U.S. Pat. No. 2,185,383 describes the reaction of 2-keto-L-gulonic acid with concentrated hydrochloric acid and acetic acid as a solvent.

JP-A 58-177986 describes a process which comprises the addition of ethanol and acetone to the sodium salt of 2-keto-L-gulonic acid, neutralization with hydrochloric acid, the removal of the precipitated sodium chloride by filtration and then the maintenance of the reaction mixture at temperatures in the range from 25° C. to 75° C., by means of which L-ascorbic acid is obtained.

JP-B 48-15931 describes the reaction of 2-keto-L-gulonic acid with a mineral acid in an inert solvent in the presence of a surface-active substance.

WO 87/00839 claims a process in which a suspension of 2-keto-L-gulonic acid is reacted to give L-ascorbic acid under acid catalysis in an inert organic solvent in the presence of a surface-active agent.

DE-A-195 47 073 describes a process for the preparation of L-ascorbic acid by reaction of 2-keto-L-gulonic acid with aqueous mineral acid in a solvent mixture comprising an inert organic solvent, an aliphatic ketone and an acid chloride.

WO 99/07691 describes the reaction of 2-keto-L-gulonic acid with concentrated hydrochloric acid at temperatures between 40 and 80° C.

EP-A-0 671 405 discloses a process for the preparation of methyl or ethyl 2-keto-L-gulonate by esterification of 2-keto-L-gulonic acid with methanol or ethanol in the presence of an acidic ion exchanger. It is furthermore to be gathered from this application that the abovementioned esters can be subjected to an alkaline rearrangement (lactonization) to give ascorbic acid or to give a salt thereof.

U.S. Pat. No. 5,391,770 describes the esterification of 2-keto-L-gulonic acid with subsequent base-catalyzed lactonization of the esters formed to give salts of L-ascorbic acid and liberation of the ascorbic acid by the addition of a strong acid.

Japanese published patent specification 22113/75 describes the esterification of 2-keto-L-gulonic acid with butanol and the subsequent acid-catalyzed lactonization in benzene as a solvent.

The abovementioned embodiments of the acid-catalyzed, single-stage process variant exhibit serious weaknesses. Thus, as a rule the use of an inert solvent is unavoidable in order to suppress the secondary reactions of the ascorbic acid with aqueous hydrochloric acid. At the same time, however, the problem is thus, however, also exchanged that the 2-keto-L-gulonic acid is always present undissolved in the form of a suspension at the start and in the course of the reaction and reaction only takes place on the crystal surface. The addition of surface-active substances alters the course of the reaction only slightly. What is more, this auxiliary can only be removed from the crude product with difficulty and means additional working-up steps in order to obtain the desired purity of the L-ascorbic acid. Long reaction times and accordingly large apparatus volumes are furthermore disadvantageous.

It was therefore the object to make available a process for the preparation of L-ascorbic acid which does not have the abovementioned disadvantages.

This object was achieved by a process for the preparation of L-ascorbic acid which comprises lactonizing a melt of $C_3$–$C_{10}$-alkyl 2-keto-L-gulonate under acidic conditions.

In a preferred embodiment, the process according to the invention furthermore comprises a) esterifying 2-keto-L-gulonic acid or 2,3:4,6-di-O-isopropylidene-2-keto-L-gulonic acid in the presence of an acidic catalyst using a $C_3$–$C_{10}$-alcohol, b) distilling off the excess $C_3$–$C_{10}$-alcohol together with the water of reaction formed and c) then lactonizing the $C_3$–$C_{10}$-alkyl 2-keto-L-gulonate formed in the form of an anhydrous melt under acidic conditions.

In the course of the process according to the invention, 2-keto-L-gulonic acid or 2,3:4,6-di-O-isopropylidene-2-keto-L-gulonic acid is first reacted to give the alkyl ester in a single-stage esterification step in the presence of an acidic catalyst. The esterification is carried out in a temperature range from –10 to 160° C., preferably from 20 to 100° C., particularly preferably in a temperature range from 40 to 90° C.

Advantageously, higher alkyl esters of saturated, branched or unbranched alkyl alcohols having a hydrocarbon number of greater than or equal to 3, preferably having an alkyl radical of 3 to 10 carbon atoms, are suitable for the esterification, such as, for example, n-propanol, isopropanol, 1-butanol, 2-butanol, 2-methyl-1-propanol, 2-methyl-2-propanol, 1-pentanol, 2-pentanol, 3-pentanol, 1-hexanol, 2-hexanol, 1-heptanol, 2-heptanol, 1-octanol, 2-octanol, 3-octanol, 1-nonanol, 2-nonanol, 1-decanol, 2-decanol, 4-decanol.

Those alcohols in which L-ascorbic acid is poorly soluble are preferably employed for the esterification. Those particularly preferably suitable are $C_4$–$C_8$ alcohols, selected from the group consisting of n-propanol, isopropanol, 1-butanol, 2-methyl-1-propanol, 2-methyl-2-propanol, 1-pentanol, 1-hexanol and 1-octanol and 1-butanol and 1-pentanol.

The alcohol is employed here in a 2- to 10-fold, preferably 3- to 6-fold, molar excess, based on the 2-keto-L-gulonic acid or 2,3:4,6-di-O-isopropylidene-2-keto-L-gulonic acid employed.

2-Keto-L-gulonic acid is preferably employed for the synthesis as a starting material. The acid can be employed here either in crystalline form, for example as a dried or centrifuge-moist monohydrate or as an anhydrous compound or as an aqueous solution, for example as a concentrated fermentation solution.

As a rule, the monohydrate of 2-keto-L-gulonic acid is obtained an crystallization from water or water-containing, organic solvents. By centrifuging off the crystal magma, moist monohydrate is accessible. This can be employed directly in the subsequent esterification reaction as a centrifuge-moist product or dried under mild conditions.

It is also possible to employ a concentrated aqueous solution of the 2-keto-L-gulonic acid directly in the esterification reaction. The excess solvent is removed before or during the esterification reaction, e.g. by extraction and phase separation or azeotropic distillation. This procedure is particularly suitable for a ketogulonic acid solution from a fermentative preparation process. After removal of the biomass by standard processes known per se, the fermentation solution, which is usually colored, can preferably be employed directly without further purification after liquid-liquid extraction. The excess solvent is then removed, as described above, before or during the esterification reaction, e.g. by phase separation or azeotropic distillation.

Anhydrous 2-keto-L-gulonic acid is obtained, inter alia, from the crystalline, optionally centrifuge-moist monohydrate using intensified drying conditions.

The drying or dehydration of the monohydrate of 2-keto-L-gulonic acid can advantageously be dispensed with in the process according to the invention, as in the subsequent activation reaction according to the invention an azeotropic dehydration is carried out anyway.

The esterification reaction is catalyzed by addition of a 0.005 to 0.1 molar, preferably of a 0.005 to 0.05 molar, amount of an acidic catalyst, in free or polymer-bound form (as strongly acidic cation exchanger) or of its ester. The description "acidic cation exchanger" is understood as meaning commercially obtainable resins, such as, for example, Lewatit® S 100 and SP 112 (Bayer) or Amberlite® 18 and IRA 120 or Amberlyst® 15 or Duolite® C 20, C 26 and C 264 (Rohm & Haas) or Dowex® ion exchanger.

Further catalysts which are suitable are also acids and their derivatives. These include, for example, phosphoric acid, monobutyl phosphate, dibutyl phosphate, monopentyl phosphate, dipentyl phosphate, sulfuric acid, monobutyl sulfate, monopentyl sulfate, hydrogen chloride, p-toluenesulfonic acid, methane-sulfonic acid, chlorosulfonic acid, trifluoroacetic acid and other strong, anhydrous acids.

2-Keto-L-gulonic acid, 2,3:4,6-di-O-isopropylidene-2-keto-L-gulonic acid or L-ascorbic acid can also be employed as acidic esterification catalysts.

However, sulfuric acid, methanesulfonic acid or monoalkyl sulfates of the $C_3$–$C_{10}$-alcohols used are preferably used; sulfuric acid may particularly preferably be mentioned. The monoalkyl sulfates eliminate sulfuric acid at temperatures above 70° C. [Popelier, Bull. Soc. Chim. Belg. 35, 265 (1926)], which acts catalytically. On use of these catalysts esterification is therefore usually only possible at relatively high temperatures.

In order to achieve a conversion which is as complete as possible during the esterification, it is advantageous to remove the water of reaction as completely as possible. In the present process, the water of reaction is advantageously distilled off with excess alcohol. This is carried out in a pressure range from 20 mbar up to normal pressure, preferably in a range from 100 to 800 mbar. The alcohol serves here as an entraining agent for the water of reaction formed. Alcohols having less than 3 carbon atoms are not as highly suitable for this. After the removal of the water by phase separation, distillative drying or drying by dehydrating agents, such as, for example, molecular sieves, the distillate is used for further esterification reactions.

The solvent used for removing water is advantageously the esterification alcohol or a mixture of this alcohol and a further water-immiscible solvent. The alcohols to be used according to the invention have only a limited capacity for eliminating the water of reaction. Particularly in the case of high catalyst acid concentrations or short esterification times, it is advantageous if a second solvent is added as a water-entraining agent as early as during the esterification reaction. This solvent should form a low-boiling azeotrope with water and optionally be only limitedly miscible with the alcohol, in order thus to be able to recycle the alcohol during the esterification reaction after phase separation. Only small amounts of this second solvent, advantageously 10 to 50 mol % based on 2-keto-L-gulonic acid, are needed.

Nonpolar halogenated hydrocarbons, such as, for example, carbon tetrachloride, chloroform, dichloroethane, 1,2-trichloroethylene, perchloroethylene or aromatic hydrocarbons, such as toluene or xylene, are advantageously employed for this. In addition, propylene carbonate can also be used. Perchloroethylene may be mentioned as the preferred solvent.

The degree of conversion of the 2-keto-L-gulonic acid in the esterification reaction is clearly over 90%, preferably in a range from 95 to 99%, in the process according to the invention.

The 2-keto-L-gulonic acid goes into solution in the course of the esterification reaction, which is a good visual indicator of the progress of the reaction. Depending on the amount of the catalyst acid employed, this takes place in a period of time of a few minutes to several hours. Higher temperatures, e.g. in the range from 30 to 150° C., favor the conversion during the esterification reaction. Toward the end of the reaction, when a major part of the excess alcohol has been distilled off, the reaction mixture becomes more viscous. The esterification reaction can advantageously be considered as complete if a solvent-free and anhydrous melt of the corresponding alkyl keto-L-gulonate results. The viscosity of this melt is dependent on the substance properties of the respective 2-keto-L-gulonic acid ester and the temperature.

On cooling, the reaction mixture solidifies in a temperature range from 20 to 40° C. The melt reforms reversibly and without decomposition on warming. Fresh addition of dry alcohol to complete the esterification reaction, as described, for example, in WO 99-3853, is not necessary under the abovementioned conditions, because a) the esterification reaction takes place almost completely and b) a 100% conversion is not absolutely necessary according to the teaching of the present invention. When using the monohydrate of keto-L-gulonic acid, a higher amount of alcohol is not necessary at the start of the esterification. The esterification rate is determined by the residual water content of the recycled alcohol.

Instead of 2-keto-L-gulonic acid, 2,3:4,6-di-O-isopropylidene-2-keto-L-gulonic acid can also be esterified in the same way under the abovementioned conditions. Removal of the acetone protective groups additionally takes place here. Two molar equivalents of water are needed for the removal, while one molar equivalent of water is simultaneously formed in the esterification reaction. This means that instead of dehydrating agents and physical drying processes chemical reactions can also be employed for removing the water of reaction. Most simply, the monohydrate of 2,3:4,6-di-O-isopropylidene-2-keto-L-gulonic acid is therefore employed. The reaction is likewise carried out in the pressure and temperature range described above.

As a low-boiling component, the acetone formed is distilled off at the start or together with the excess, water-containing solvent during the esterification reaction and can be recycled after isolation and recovery in pure form.

The esterification reaction of 2-keto-L-gulonic acid or 2,3:4,6-di-O-isopropylidene-2-keto-L-gulonic acid can be operated batchwise or continuously. In the case of continuous esterification, the azeotropic distillation is carried out, for example, in a stirring vessel cascade, a thin-film evaporator or in similarly operating equipment. Even under these conditions, a molten form of the corresponding alkyl 2-keto-L-gulonate is formed at the end of the esterification. In comparison with the batchwise esterification, the advantage of this procedure is that the reaction time is markedly under 1 hour with the same conversion and same purity.

In the preferred embodiment of the process according to the invention, after process steps a) and b) a melt or molten form of the ester is obtained which is highly fluid and can easily be transported in pipelines. This melt can be rearranged without isolation or without further purification to give L-ascorbic acid of high purity with liberation of the alcohol used for the activation, either under 100° C. at normal pressure, if appropriate in an inert solvent, such as, for example, a halogenated hydrocarbon, in the presence of an acidic catalyst, such as, for example, hydrochloric acid, or over 90° C. at elevated pressure in the presence of small amounts of water without a further organic solvent, if appropriate in the presence of an acidic catalyst, such as, for example, hydrogen chloride.

Following the esterification reaction of the 2-keto-L-gulonic acid or 2,3:4,6-di-O-isopropylidene-2-keto-L-gulonic acid, in process step c) the rearrangement (lactonization) of the ester formed—in the form of its melt—to give L-ascorbic acid takes place in the presence of an acidic catalyst. An anhydrous melt is preferably employed here.

The present invention relates here to two different procedures for the manner of this rearrangement. The rearrangement can be carried out at lower temperatures and with longer reaction times in the presence of an additional inert solvent or directly at higher temperatures without the aid of inert solvents, but if appropriate in the presence of water.

It is known that the ascorbic acid reacts to give undesired, dark-colored by-products, for example during the rearrangement with aqueous hydrochloric acid [Crawford et al., Adv. Carbohydrate Chem. 37, 79–155 (1980)], if it is not removed from the reaction mixture immediately after its formation. As a rule, this is carried out in the conventional solvent procedure by addition of an inert solvent in which the ascorbic acid is insoluble or poorly soluble. Taking into account this fact, it is understandable that in the processes known from the literature difficulties frequently occur on the industrial scale, because the precipitating ascorbic acid leads only to mixtures or wax-like masses which are difficult to stir and not easy to handle. In particular, small amounts of undesired catalyst acid are included in this procedure during the crystallization process, which mostly proceeds via an amorphous solid. Even in traces in the final product, these residual amounts of unremoved catalyst acid lead to poorer qualities and therefore usually require an uneconomically high expenditure on purification.

When employing an ester of 2-keto-L-gulonic acid, equivalent amounts of alcohol are liberated from the ester again in the course of the reaction during the acid-catalyzed rearrangement. On the one hand, the reaction product, L-ascorbic acid, is poorly soluble according to the invention in the alcohol and on the other hand the catalyst acid as well as small amounts of by-products, however, are more readily soluble. If the rearrangement of the ester is carried out from the start in an inert solvent, then the purification effect of the inert solvent can be significantly increased by the liberated alcohol.

Suitable alcohols for this are advantageously the same higher alcohols according to the invention as are employed for the esterification of the ketogulonic acid. These are, in particular, alcohols having a carbon number of greater than or equal to 3, such as, for example, n-propanol, isopropanol, n-butanol, isobutanol, 1-pentanol, 2-pentanol, 3-pentanol, 1-hexanol, 2-hexanol, 1-heptanol, 2-heptanol, 1-octanol, 2-octanol, 3-octanol, 1-nonanol, 2-nonanol, 1-decanol, 2-decanol, 4-decanol etc.

The nonpolar, inert solvents which are preferred for rearrangement in solution also have already been described above. Nonpolar halogenated hydrocarbons, such as, for example, carbon tetrachloride, chloroform, dichlorethane, 1,2-trichloroethylene, perchloroethylene or aromatic hydrocarbons, such as toluene, chlorobenzene or xylene, are preferably employed. Perchloroethylene is particularly preferred. Cyclic carbonates, such as, for example, propylene carbonate, can also be employed with good success.

The rearrangement is carried out according to process variant a) in solution in a temperature range from 40 to 100° C., preferably between 50 and 95° C. The reaction time here must be tailored to the corresponding rearrangement temperature. The reaction times are in the abovementioned temperature range at normal pressure, preferably between 0.25 and 20 hours. Under these conditions, high yields and high purities of L-ascorbic acid are achieved.

The catalyst acid employed is of crucial importance for the success of the rearrangement reaction. Mineral acids, such as, for example, phosphoric acid or sulfuric acid, are suitable. Hydrogen chloride is advantageously employed, either as concentrated aqueous hydrochloric acid or as a gas which is directly passed into the rearrangement mixture. Water is needed for the rearrangement. The necessary amount of water must therefore be added when employing hydrogen chloride. It is advantageous not to introduce the water of reaction into the rearrangement step via the esterification stage. Too high an acid concentration in the presence of water causes lower yields of valuable product and poorer purities. A concentration of 1 to 5% based on hydrogen chloride gas in the mixture of higher alcohol and the inert solvent indicated above is preferably employed.

The catalyst acid can be introduced into the rearrangement reactor with the inert solvent or added to the rearrangement mixture.

For longer rearrangement times at lower temperatures according to the invention, as a rule the molten form of the alkyl 2-keto-L-gulonate is preferably allowed to run into the introduced inert solvent together with the catalyst acid or the reaction is carried out conversely. In all cases, adequate mixing of the acid with the reaction mixture is important for the success of the rearrangement. The L-ascorbic acid formed precipitates in crystalline form toward the end of the rearrangement and can be isolated by customary processes, such as, for example, filtering off with suction, centrifuging off, squeezing off or extraction. After washing with the alcohol which was also employed for the esterification, and drying, the vitamin C is obtained as a crude product in high purities (98.5 to 99.8%) and yields (87 to 93%). This manner of conducting the reaction has a side effect which is surprising for the person skilled in the art and which has a significant effect on the purity and yield of the reaction product. In this rearrangement, small amounts of activated carbon in finely divided form, which adsorb traces of undesired by-products and can easily be removed mechanically, are advantageously additionally produced in situ in a controlled manner. Laborious purification of the resulting L-ascorbic acid is thus superfluous. The proportion of activated carbon is in the range from 0.1 to at most 0.8%. These amounts are sufficient for the effective adsorption of, for example, colored impurities which can originate, inter alia, from 2-keto-L-gulonic acid prepared by fermentation. The carbon formed can be conveniently removed in the course of the isolation of the ascorbic acid.

The yield and purity of vitamin C is significantly influenced by the composition of the solvent mixture in the course of the rearrangement. Too high a concentration of water reduces the yield. The water content in this mixture should therefore be in the range from 1 to 10%, preferably in the range from 2 to 7%. Toward the end of the rearrangement, the rearrangement mixture advantageously contains 50 to 90% by weight of the inert solvent and 50 to 10% by weight of the alcohol formed. In this mixture, L-ascorbic acid is poorly soluble and all other starting materials or by-products and the catalyst acid are readily soluble.

The alkyl 2-ketogulonate melt can be rearranged according to process variant b) mentioned above even without employing an inert solvent. Here, the esterification alcohol is liberated in the course of the reaction and brings about the formation of a finely divided, pumpable crystal suspension of the L-ascorbic acid. This type of rearrangement in the presence of the preferred catalyst acid hydrogen chloride or hydrochloric acid takes place in a significantly shorter time than already described in process variant a). According to the invention, the addition of the inert, organic solvent is dispensed with here. The presence of water, however, is advantageous according to the invention.

According to the invention, the melt or molten form of the alkyl 2-keto-L-gulonate is rapidly mixed here, at temperatures between 20 and 100° C., with the catalyst acid and then subjected to a brief rearrangement at a temperature between 95 and 160° C., preferably between 100 and 140° C. This rearrangement reaction is advantageously carried out at a pressure of 0.5 to 10 bar. The residence time in the reactor, which can be designed, for example, as a tubular reactor, is preferably in the range from a few seconds up to 1 hour. In this type of rearrangement, which according to the invention can preferably also be operated continuously, the alcohol is eliminated and then evaporated at reduced pressure such that an establishment of equilibrium between vapor and liquid and a subsequent reaction of the L-ascorbic acid with the catalyst acid is avoided as completely as possible. By releasing the pressure in vacuo, the catalyst acid is removed at a high evaporation rate and at the same time L-ascorbic acid precipitates in the alcohol in finely divided form. The liberated alcohol can be recovered according to known processes and used again for the ester synthesis. The crude ascorbic acid formed from this rearrangement reaction as a residue has a purity of greater than 98% and can be supplied directly to one of the customary purification processes either as a solid or in solution. The yield according to this process variant is 90 to 95%.

The process according to the invention is intended to be illustrated in greater detail by means of the following examples.

The yields and purities of the experiments described relate to isolated, dried vitamin C. The yield data are based on mol %. The purity of the 2-keto-L-gulonic acid and the diacetone-2-keto-L-gulonic acid was measured by HPLC calibrated against a reference sample. The content of vitamin C was determined in the crude product using the customary iodometric titration method.

EXAMPLE 1

742 g (3.75 mol) of anhydrous 2-keto-L-gulonic acid were suspended in 1.5 l (17 mol) of n-butanol and, after addition of 8 g of concentrated sulfuric acid, the mixture was evacuated to 200 mbar. After heating to 85° C., 1.1 l of water-containing n-butanol were distilled off after 2 hours. The viscous, golden-yellow-colored melt was mixed with 906 ml (8.9 mol) of perchloroethylene and rearranged at 72 to 75° C. for 17 hours after addition of 84 ml of conc. hydrochloric acid. The precipitated L-ascorbic acid was filtered off with suction, washed with n-butanol and dried in vacuo. 588 g (88%) of a pale gray crude product having a purity of 98.5% were obtained. The crude product dissolved in water. After clarifying filtration, a colorless solution was obtained from which it was possible to isolate L-ascorbic acid in a manner known from the literature. The residue (0.9%) consisted mainly of carbon.

EXAMPLE 2

According to Example 1, 2-keto-L-gulonic acid monohydrate was employed instead of anhydrous 2-keto-L-gulonic acid. The esterification time increased only insignificantly. The amount of the water distilled off increased correspondingly in the distillate. The yield of L-ascorbic acid (crude product) was 87.5% (purity 98.9%).

EXAMPLE 3

According to Example 1, a 40% strength by weight aqueous 2-keto-L-gulonic acid solution (based on anhydrous acid) was employed instead of anhydrous 2-keto-L-gulonic acid. The esterification time increased by 45 min. The amount of water distilled off likewise increased by the amount additionally employed. The yield of L-ascorbic acid (crude product) was 87.3% (purity 98.6%).

EXAMPLE 4

Esterification and rearrangement were carried out in analogy to Example 1. The difference, however, consisted in the fact that the golden-yellow esterification mixture was stirred into perchloroethylene/hydrochloric acid. The yield of dried crude product was 89% (purity 99.5%).

EXAMPLE 5

Esterification and rearrangement were carried out according to Example 1. The precipitated L-ascorbic acid was extracted twice with a total of 450 ml of water and purified after clarifying filtration. 87% of L-ascorbic acid having a purity of 99% were found in the aqueous solution after careful evaporation.

EXAMPLE 6

594 g (3 mol) of anhydrous 2-keto-L-gulonic acid were suspended in a solvent mixture consisting of 72 ml (0.7 mol) of perchloroethylene and 1 l (11 mol) of n-butanol. After addition of 7 g (69 mmol) of conc. sulfuric acid, the mixture was evacuated to 300 mbar and heated to an internal temperature of 85° C. The distillate was removed. After 2 hours, 24 ml of water were removed. After addition of 725 ml (7 mol) of fresh perchloroethylene, the viscous reaction mixture was rapidly treated with 79 g (0.8 mol) of conc. hydrochloric acid and stirred at 75° C. for 17 hours. The precipitated L-ascorbic acid was filtered off with suction, washed with n-butanol and dried in vacuo. Yield: 460 g (86%) of a gray crystallizate having a vitamin C purity of 99%. Vitamin C of high purity can be obtained by processes known from the literature, e.g. recrystallization.

EXAMPLE 7

584 g (2 mol) of diacetone-2-keto-L-gulonic acid monohydrate were suspended in 667 g (9 mol) of n-butanol and the mixture was evacuated to 200 mbar after addition of 5 g of conc. sulfuric acid. After heating to 85° C., 580 g of acetone- and water-containing n-butanol were distilled off after 2 hours. The viscous, golden-yellow-colored melt was mixed with 906 ml (8.9 mol) of perchloroethylene and subjected to rearrangement at 72 to 75° C. for 17 hours after addition of 84 ml of conc. hydrochloric acid. The precipitated L-ascorbic acid was filtered off with suction, washed with n-butanol and dried in vacuo. 580 g (87%) of a pale gray crude product having a purity of 98.6% were obtained.

EXAMPLE 8

In accordance with Example 1, the esterification reaction was operated continuously. The viscous, golden-yellow-colored melt was pumped into a tubular reactor heated to 107° C. at 72° C. in a continuous flow of 12.4 kg/hour together with 0.1 mol of 37% strength hydrochloric acid/hour. A pressure of 7.2 bar was established in the steady-state operation. After a residence time of 4 min, the reaction mixture was depressurized at a temperature of 32° C. in a thin-film evaporator operated at 20–50 mbar, from which an aqueous, almost colorless solution of L-ascorbic acid was isolated in the bottom. After further cooling, this was fed directly to purification and crystallization. Content determination of a sample of the material discharged from the reaction showed a yield of L-ascorbic acid of 87.5% having a purity of 98.3%. The distillate removed over the top in the thin-film evaporator was redistilled after condensation and the recovered alcohol was used again for the esterification.

We claim:

1. A process for the preparation of L-ascorbic acid, which comprises lactonizing a melt of $C_3$–$C_{10}$-alkyl 2-keto-L-gulonate under acidic conditions.

2. A process as claimed in claim 1, wherein the lactonization is carried out in an inert, water-immiscible solvent in the presence of a mineral acid.

3. A process as claimed in claim 1, wherein the lactonization is carried out in a halogenated hydrocarbon in the presence of aqueous hydrochloric acid.

4. A process as claimed in claim 3, wherein the inert solvent used is a halogenated hydrocarbon selected from the group consisting of dichloromethane, chloroform and perchloroethylene.

5. A process as claimed in claim 1, wherein
   a) 2-keto-L-gulonic acid or 2,3:4,6-di-O-isopropylidene-2-keto-L-gulonic acid is esterified in the presence of an acidic catalyst using a $C_3$–$C_{10}$-alcohol,
   b) the excess $C_3$–$C_{10}$-alcohol is distilled off together with the water of reaction formed and
   c) then the $C_3$–$C_{10}$-alkyl 2-keto-L-gulonate formed is lactonized in the form of an anhydrous melt under acidic conditions.

6. A process as claimed in claim 5, wherein the esterification in process step a) is carried out using an alcohol selected from the group consisting of n-propanol, isopropanol, 1-butanol, 2-butanol, 2-methyl-1-propanol, 2-methyl-2-propanol, 1-pentanol, 1-hexanol and 1-octanol.

7. A process as claimed in claim 5, wherein the esterification in process step a) is carried out in the presence of a mineral acid or of an acidic ion exchanger.

8. A process as claimed in claim 5, wherein the esterification in process step a) is carried out with n-butanol in the presence of sulfuric acid.

9. A process as claimed in claim 5, wherein the esterification in process step a) is carried out in an inert, water-immiscible solvent.

10. A process as claimed in claim 5, wherein the starting material used is 2-keto-L-gulonic acid.

11. A process as claimed in claim 5, wherein the reaction temperatures in process steps a) to c) are in the range from −10 to 160° C.

12. A process as claimed in claim 5, wherein the esterification and lactonization in process steps a) to c) are carried out at pressures in the range from 0.1 to 10 bar.

13. A process as claimed in claim 5, wherein the ester formed in process steps a) and b) is employed directly in the lactonization stage without isolation and purification.

* * * * *